(12) United States Patent
Adachi (10) Patent No.: US 9,303,272 B2
(45) Date of Patent: Apr. 5, 2016

(54) GENE TARGETING VECTOR, AND METHOD FOR USING SAME

(71) Applicant: PUBLIC UNIVERSITY CORPORATION YOKOHAMA CITY UNIVERSITY, Yokohama-shi, Kanagawa (JP)

(72) Inventor: Noritaka Adachi, Yokohama (JP)

(73) Assignee: PUBLIC UNIVERSITY CORPORATION YOKOHAMA CITY UNIVERSITY, Yokohama-Shi (JP)

( * ) Notice: Subject to any disclaimer, the term of this patent is extended or adjusted under 35 U.S.C. 154(b) by 24 days.

(21) Appl. No.: 14/364,922

(22) PCT Filed: Dec. 12, 2012

(86) PCT No.: PCT/JP2012/082160
§ 371 (c)(1),
(2) Date: Jun. 12, 2014

(87) PCT Pub. No.: WO2013/089123
PCT Pub. Date: Jun. 20, 2013

(65) Prior Publication Data
US 2014/0335621 A1    Nov. 13, 2014

(30) Foreign Application Priority Data
Dec. 13, 2011    (JP) ................ 2011-272072

(51) Int. Cl.
| | |
|---|---|
| C12N 15/00 | (2006.01) |
| C12N 5/00 | (2006.01) |
| C12N 15/85 | (2006.01) |
| C12N 15/09 | (2006.01) |
| C12N 15/90 | (2006.01) |
| C12N 15/63 | (2006.01) |

(52) U.S. Cl.
CPC ............. *C12N 15/85* (2013.01); *C12N 15/09* (2013.01); *C12N 15/8509* (2013.01); *C12N 15/907* (2013.01); *C12N 15/63* (2013.01); *C12N 2830/50* (2013.01); *C12N 2840/203* (2013.01); *C12N 2840/44* (2013.01)

(58) Field of Classification Search
USPC .............................. 435/320.1, 325
See application file for complete search history.

(56) References Cited

U.S. PATENT DOCUMENTS

| | | | | |
|---|---|---|---|---|
| 5,922,601 | A | * 7/1999 | Baetscher | .......... C12N 15/1051 435/320.1 |
| 6,150,169 | A | 11/2000 | Smith et al. | |
| 6,284,541 | B1 | 9/2001 | Auer et al. | |
| 2009/0241207 | A1 | 9/2009 | Lathe | |

FOREIGN PATENT DOCUMENTS

| | | |
|---|---|---|
| CN | 1276836 A | 12/2000 |
| GB | WO 94/24301 | * 10/1994 |
| JP | 9-500005 A | 1/1997 |
| WO | WO 03/044203 A2 | 5/2003 |
| WO | WO 2004/042007 A2 | 5/2004 |
| WO | WO 2004/072251 A2 | 8/2004 |

OTHER PUBLICATIONS

CN 1276836 Machine translation, 2000.*
CN 2012800660477 search report, 2012.*
CN 2012800660477 search report translation, 2012.*
Adachi et al., "Gene targeting using the human Nalm-6 pre-B cell line", BioScience Trends, vol. 2, No. 5, Oct. 2008, XP-55201791, pp. 169-180.
Extended European Search Report, dated Jul. 22, 2015, for European Application No. 12857876.2.
Guo et al., "The Rapid Construction of Rabbit HPRT Promoterless Gene-targeting Vector with PCR Product", Laboratory Animal and Comparative Medicine, vol. 29, Issue 2, 2009, pp. 86-92, abstract only provided.
Ono et al., "Generation of tetracycline-inducible conditional gene knockout cells in a human Nalm-6 cell line", Journal of Biotechnology, vol. 141, Apr. 20, 2009, pp. 1-7.
English translation of International Preliminary Report on Patentability issued Jun. 13, 2014, in PCT International Application No. PCT/JP2012/082160.
International Search Report for PCT/JP2012/082160 mailed on Mar. 12, 2013.

* cited by examiner

*Primary Examiner* — Michael Wilson
(74) *Attorney, Agent, or Firm* — Birch, Stewart, Kolasch & Birch, LLP (57) ABSTRACT

Provided is a gene targeting vector that enables highly efficient gene targeting. The gene targeting vector has a structure comprising a positive selection marker flanked by a DNA homologous to a 5'-upstream region of a target site and a DNA homologous to a 3'-downstream region of the target site, wherein a splice acceptor site and a DNA sequence allowing for bicistronic expression are added 5'-upstream of the positive selection marker, and another splice acceptor site is also added 5'-upstream of the DNA homologous to the 5'-upstream region of the target site.

6 Claims, 4 Drawing Sheets

Fig.3 attB4-containing prim : 5'-GGGGACAACTTTGTATAGAAAAGTTGNNNNNNNNNNNNNNNNNNNNNNNNN-3' attB1-containing prim : 5'-GGGGACTGCTTTTTTGTACAAACTTGNNNNNNNNNNNNNNNNNNNNNNNNN-3' attB2-containing prim : 5'-GGGGACAGCTTTCTTGTACAAAGTGGNNNNNNNNNNNNNNNNNNNNNNNNN-3' attB3-containing prim : 5'-GGGGACAACTTTGTATAATAAAGTTGCTAT ATTACCCTGTTATCCCTA NNNNNNNNNNNNNNNNNNNNNNNNN-3'
I-SceI si

GENE TARGETING VECTOR, AND METHOD FOR USING SAME

TECHNICAL FIELD

The present invention relates to a gene targeting vector and a method for using the same.

BACKGROUND ART

It is possible to disrupt a gene(s) on the genome or replace it with a transfected DNA fragment by utilizing a cell's ability for homologous recombination (Non-Patent Literatures 1 and 2). This technique is referred to as gene targeting. This technique has not only been a powerful tool for the analyses of the functions of individual genes, but is also anticipated to be used as an ideal gene therapy or breeding method (Non-Patent Literature 3). However, the efficiency of gene targeting in common higher animal or plant cells is extremely low, and thus, it has been desired to develop an improved method that copes with this difficulty. Use of an exon-trapping-type targeting vector having a promoter-free marker gene has been shown to reduce the frequency of occurrence of random insertion, probably leading to enhanced gene targeting efficiency (Non Patent Literatures 4 and 5). Nonetheless, the marker gene may be expressed even by random insertion into a non-target gene. Thus, it has been desired to develop improved methods toward more efficient gene targeting.

CITATION LIST

Non Patent Literature

Non Patent Literature 1: Capecchi, M R (1989) Altering the genome by homologous recombination. Science 244: 1288-1292

Non Patent Literature 2: Vasquez K M, Marburger K, Intody Z, et al. (2001) Manipulating the mammalian genome by homologous recombination. Proc. Natl. Acad. Sci. USA 98: 8403-8410

Non Patent Literature 3: Yanez R J, Porter A C (1998) Therapeutic gene targeting. Gene Ther 5: 149-159

Non Patent Literature 4: Bunz F, Dutriaux A, Lengauer C, et al. (1998) Requirement for p53 and p21 to Sustain G2 Arrest After DNA Damage. Science 282: 1497-1501

Non Patent Literature 5: Adachi N, So S, Iiizumi S, et al. (2006) The human pre-B cell line Nalm-6 is highly proficient in gene targeting by homologous recombination. DNA Cell Biol. 25: 19-24

DISCLOSURE OF THE INVENTION

Problems to be Solved by the Invention

An object of the present invention is to provide a gene targeting vector capable of highly efficient gene targeting.

In addition, another object of the present invention is to provide a method for producing a gene knockout cell line with the use of a gene targeting vector capable of highly efficient gene targeting.

Means for Solving the Problems

The primary cause of the low efficiency of gene targeting is that a targeting vector introduced into a cell is inserted into a random site on the genome at a high frequency (random integration). However, with the use of a promoterless-type targeting vector, an increase in targeting efficiency can be expected. Thus, if such a vector, in particular, an exon-trapping-type targeting vector can be produced simply and promptly, certain technological innovation should be achieved.

The present inventor developed a technique of improving gene targeting efficiency by adding a DNA sequence allowing for bicistronic expression, such as an IRES sequence or a 2A sequence, to a position 5' upstream of a selection marker in the gene targeting vector (e.g., an exon-trapping-type targeting vector) (Japanese Patent Application No. 2011-118564, filed on May 27, 2011).

Figure 4:
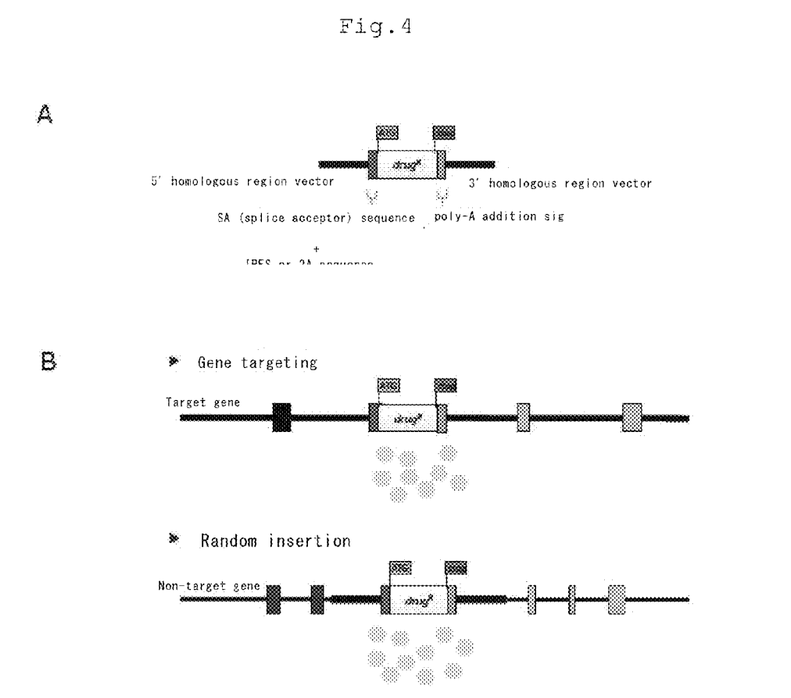
FIG. 4 shows gene targeting using an exon-trapping-type targeting vector disclosed in Japanese Patent Application No. 2011-118564.

The gene targeting vector disclosed in Japanese Patent Application No. 2011-118564, however, produces less than sufficient effects of negative selection, because a marker gene (positive selection marker gene) used in screening is expressed not only in a correctly targeted clone but also in clones with random insertions in non-target genes (FIGS. 4A and 4B).

Figure 5:
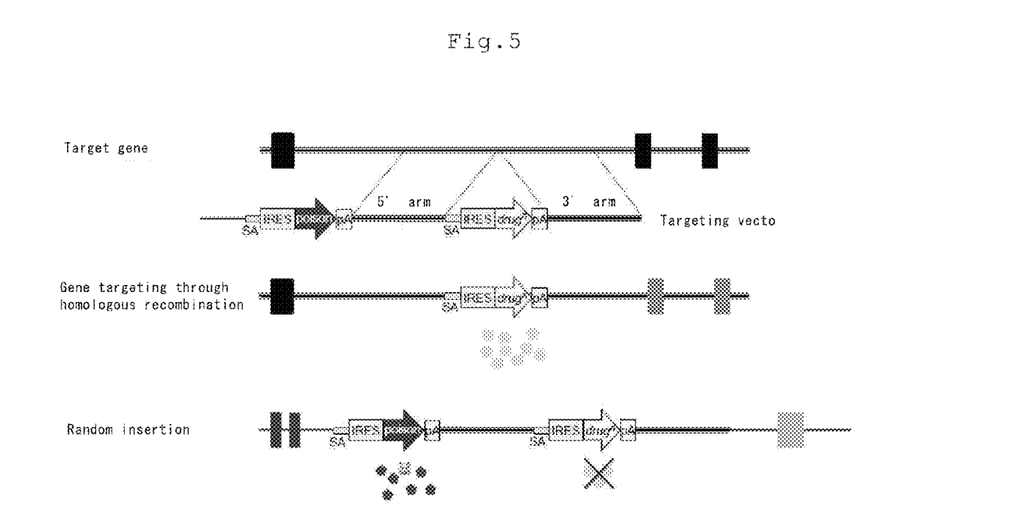
FIG. 5 shows gene targeting by the ExTraPNS method using a newly developed exon-trapping-type targeting vector that possesses a cassette for negative selection (the vector shown in the upper diagram of FIG. 6 will be taken as an example). The addition of a suicide gene having a splice acceptor sequence upstream of a 5'-homologous region considerably decreases the possibility that the positive selection marker gene is expressed in randomly inserted clones. When gene-targeting via homologous recombination occurs, the cassette for negative selection is not inserted into the genome. For this reason, gene targeting efficiency is significantly enhanced. In this context, similar effects can be expected by adding the splice acceptor sequence upstream of the 5'-arm (see the vector shown in the lower diagram of FIG. 6), even if the gene serving as the negative selection marker is not added thereto.

The present inventor has successfully achieved a further improvement in gene targeting efficiency by adding a negative selection marker (e.g., a suicide gene) having a splice acceptor sequence at a position upstream of a 5' target site-homologous region in the gene targeting vector disclosed in Japanese Patent Application No. 2011-118564; as a result, the positive selection marker gene is prevented from being expressed in clones with random insertions and this has led to the completion of the present invention (FIG. 5). The present invention is expected to confer similar effects (i.e., the prevention of the marker gene used in screening from being expressed in randomly inserted clones) by adding the splice acceptor sequence at a position upstream of the 5' target site-homologous region, even if the gene serving as the negative selection marker is not added to the gene targeting vector. This approach of the present invention has been designated as Exon-Trap Positive/Negative Selection method (ExTraPNS method).

A summary of the present invention is as follows:

(1) A gene targeting vector having a structure comprising a positive selection marker flanked by a DNA homologous to a 5'-upstream region of the target site and a DNA homologous to a 3'-downstream region of the target site, wherein a splice acceptor site and a DNA sequence allowing for bicistronic expression are added 5'-upstream of the positive selection marker, and another splice acceptor site is also added 5'-upstream of the DNA homologous to the 5'-upstream region of the target site.

(2) The vector according to (1), wherein a poly-A sequence is added to the positive selection marker, while no promoter is added thereto.

(3) The vector according to (1) or (2), wherein a poly-A sequence is added 3'-downstream of the splice acceptor site added 5'-upstream of the DNA homologous to the 5'-upstream region of the target site.

(4) The vector according to (3), wherein a negative selection marker is introduced between the splice acceptor site added 5'-upstream of the DNA homologous to the 5'-upstream region of the target site and the poly-A sequence added 3'-downstream thereof.

(5) The vector according to any of (1) to (4), wherein a restriction site(s) for linearization is further introduced in the vector.

(6) A method for preparing a gene knockout cell line, comprising introducing a genetic mutation to a cell using a gene targeting vector according to any of (1) to (5).

Advantageous Effects of Invention

The present invention has enabled gene targeting to be performed with higher efficiency than ever. The method of the present invention is particularly effective for gene targeting using an exon-trapping-type targeting vector. The present invention is effective for more versatile or more efficient gene knockout/knockin in the fields of basic biology, medicine, and agriculture and livestock industry.

The present specification encompasses the contents described in the specification and/or drawings of Japanese Patent Application No. 2011-272072 on which the priority of the present application is based.

BRIEF DESCRIPTION OF THE DRAWINGS

FIG. 1A shows a structure of a common substitution-type targeting vector. When a targeting vector is introduced into cells and colonies are allowed to form in the presence of a selective drug, homologous recombinants can be obtained in which the target site is replaced with a drug resistance gene, and non-homologous recombinants in which the targeting vector is inserted into a random site(s) on the chromosome. The non-homologous recombinants make up an overwhelming majority. That is to say, since both homologous recombinants and non-homologous recombinants have the drug resistance gene, it is difficult to obtain homologous recombinant cells by this drug selection only. However, if a suicide gene such as DT-A is added to the outside of either arm, non-homologous recombinants will die due to the expression of the suicide gene incorporated into the chromosome. Each ellipse in the figure indicates a cell, and the rectangular box like a bar in the ellipse indicates a chromosome. The thick gray region in the chromosome indicates a target site, and the light gray regions in the chromosome and the targeting vector indicate homologous regions. The region flanked with the arms of the targeting vector indicates a drug resistance gene, and the black square region indicates a DT-A gene. FIG. 1B shows an example of the structure of a promoterless-type targeting vector. Differing from the aforementioned substitution-type targeting vector, a gene to be used as a positive selection marker does not have its own promoter. Thus, theoretically, only when gene targeting by homologous recombination takes place, a target gene promoter on the chromosome is used, and the expression of a marker gene is allowed;

FIG. 2 summarizes the method to construct targeting vectors using Multisite Gateway technology. A 5'-arm and a 3'-arm each having attB sequences at both ends are amplified by PCR and then subjected to BP recombination reaction to prepare a 5'-entry clone and a 3°-entry clone (A). The obtained two entry clones, as well as pENTR IRES-Hyg and a plasmid having SA-IRES-DTA-polyA (cassette for negative selection) added to pDEST R4-R3 were used in LR recombination to construct a targeting vector (B). Hyg represents a hygromycin-resistance gene. DTA represents a diphtheria toxin A fragment gene. Km$^r$ represents a kanamycin-resistance gene. Amp$^r$ represents an ampicillin-resistance gene;

FIG. 3 shows an outline of PCR for arm amplification and primer sequences. Each arm is amplified by PCR such that it is flanked with attB sequences. The underlined portions in the primer sequences indicate respective attB sequences, N indicates a template-specific sequence, and the framed portion indicates an I-SceI recognition sequence. The template-specific sequence may have a length of approximately 25 nucleotides;

FIG. 4A shows the structure of a common substitution-type exon-trapping-type targeting vector. This vector has a positive selection marker between the 5'-arm and the 3'-arm. The positive selection marker has no promoter of its own and instead has a splice acceptor site and a DNA sequence allowing for bicistronic expression, which are located 5'-upstream of the marker?. A poly-A addition signal is added 3'-downstream of the marker?. FIG. 4B shows a problem associated with gene targeting using the exon-trapping-type targeting vector disclosed in Japanese Patent Application No. 2011-118564. The positive selection marker gene may be expressed not only in a clone with an insertion in the target gene by targeting through homologous recombination (upper diagram) but also in clones with random insertions into non-target genes (lower diagram). In particular, a clone with an insertion in a gene with high expression levels can acquire stronger drug resistance than the clone with an insertion in the target gene. For this reason, the exon trap strategy alone does not confer sufficient effects of negative selection;

BEST MODE FOR CARRYING OUT THE INVENTION

Hereinafter, the embodiments of the present invention will be described more in detail.

Figure 1:
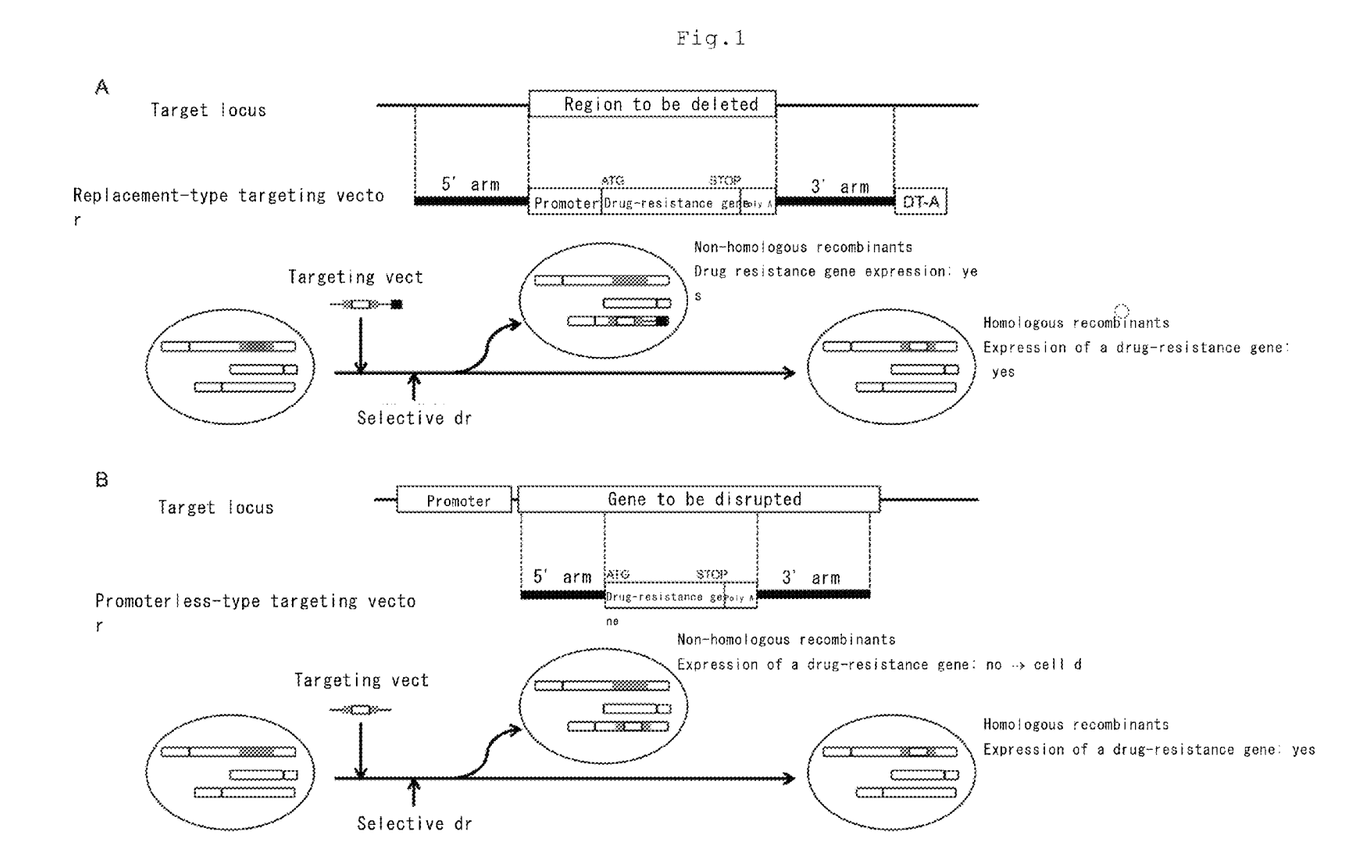
FIG. 1 shows structures of targeting vectors.

Gene targeting is a technique of introducing a mutation into any given site on the chromosome by utilizing a homologous recombination mechanism. However, the homologous recombination frequency is low in higher organisms. In general, the frequency at which a targeting vector is randomly inserted into an incorrect site in a cell is 100 or more times higher than the frequency at which the vector is inserted in a target site in the cell. Hence, in order to efficiently select and obtain homologous recombinant cells, some modifications need to be made on the targeting vector. The most commonly used substitution-type targeting vector has such a structure that a positive selection marker (a drug resistance gene in FIG. 1A) is flanked with DNA fragments that are homologous to a 5' upstream region and a 3' downstream region of the target site (a region to be deleted) (the fragments are hereinafter sometimes referred to as a "5' arm" and a "3' arm," respectively) (FIG. 1A). Examples of the positive selection marker include: drug-resistance genes such as Hyg (a hygromycin-resistance gene), Puro (a puromycin-resistance gene), and β-geo (a fusion gene of a β-galactosidase gene with a neomycin-resistance gene); fluorescent protein genes such as a GFP gene; and a luciferase gene. Since the target site is replaced with a positive selection marker upon homologous recombination, recombinant cells can be selected using this marker as an indicator. However, the expression of a marker gene does occur even if the marker is inserted randomly by non-homologous recombination. Hence, a common practice for selecting against non-homologous recombinant cells is to add a gene for negative selection to the outside of the arm in the targeting vector. Examples of such a gene for negative selection include suicide genes such as HSV-TK or DT-A. As an alternative method, a promoterless method (including an "exon trapping method") has been developed, in which a drug resistance gene (a positive selection marker) does not have a promoter (FIG. 1B). In this method, when homologous recombination takes place, the expression of a positive selection marker gene begins. Nonetheless, the expression of the positive selection marker gene may begin even by random insertion through non-homologous recombination. The ExTraPNS method of the present invention has been developed to decrease recombinants produced by the latter reaction.

Figure 2:
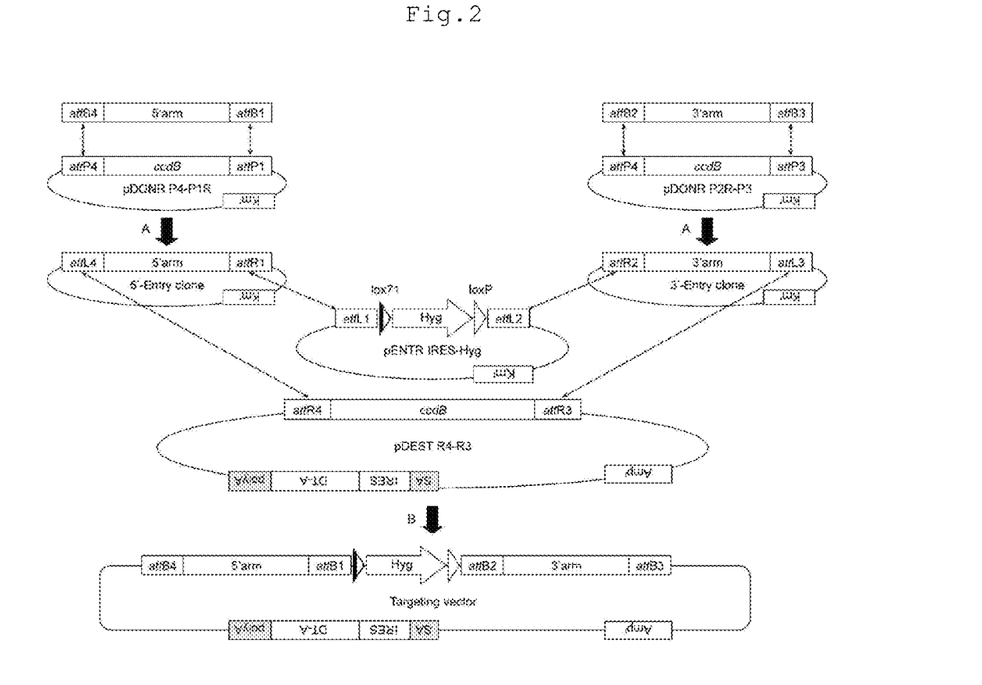

In the present specification, a method for producing a substitution-type targeting vector with the use of Multisite Gateway technology (Iiizumi, S, Nomura, Y, So, S, et al. (2006) Simple one-week method to construct gene-targeting vectors: application to production of human knockout cell lines. Biotechniques 41: 311-316) will be described as an example (FIG. 2).

Specifically, BP recombination is first carried out between a 5' arm having attB4 and attB1 sequences at the ends (corresponding to the "DNA fragment homologous to a 5' upstream region of the target site" in the present invention) and pDONR P4-P1R, and also between a 3' arm having attB2 and attB3 sequences at the ends (corresponding to the "DNA fragment homologous to a 3' downstream region of the target site" in the present invention) and pDONR P2R-P3, so as to produce a 5'-entry clone and a 3'-entry clone, respectively. (The 5' and 3' arms are preliminarily obtained by genomic PCR.)

It is recommended that a reverse primer used for amplification of the 5' arm be preliminarily designed on the exon of a target gene. In this way, an SA site (splice acceptor site) allowing for natural splicing from an upstream exon to a selection marker gene (or an exon into which this marker gene has been inserted) on the target gene can be included within the 5' arm. The SA site is not limited to the SA sequence of the target gene, and other SA sites may also be used.

Figure 3:
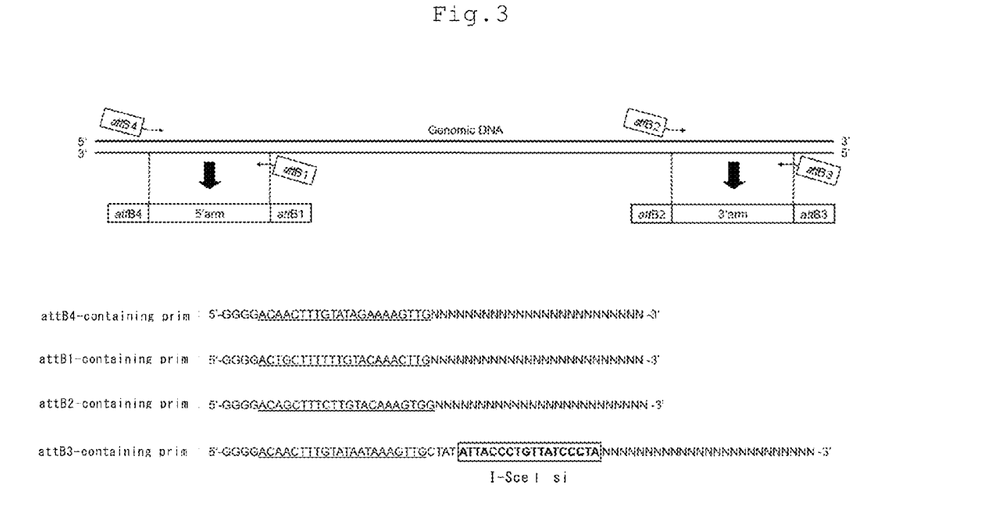

It is also recommended that a restriction site for vector linearization (e.g. I-SceI) be added to the reverse primer for 3'-arm amplification (or the forward primer for 5'-arm amplification) (FIG. 3). As a result, restriction mapping for determining restriction enzymes for linearization can be omitted.

Next, LR recombination is carried out between four components, namely, the two entry clones, pENTR IRES-Hyg prepared by introduction of a hygromycin-resistance gene flanked by attL1 and attL2 sequences, and a plasmid having a cassette for negative selection (here, SA-IRES-DTA-polyA) added to pDEST R4-R3 (Invitrogen Corp.) Only these two steps are required to complete an exon-trapping-type, substitution-type targeting vector (FIG. 2).

A DNA sequence allowing for bicistronic expression (for example, an IRES (internal ribosomal entry site, which is a site for ribosomal entry in mRNA; a site derived from encephalomyocarditis virus (EMCV), etc.) sequence, a 2A peptide sequence (a 2A "self-cleaving" peptide sequence; one derived from Thosea asigna virus (TaV), etc.), IRES2, etc.) is added 5' upstream of a hygromycin-resistance gene (other selection markers may also be used). Since the DNA sequence allowing for bicistronic expression is present 5' upstream of the selection marker, when gene targeting takes place, gene expression of the selection marker is achieved depending on the target gene promoter.

It is recommended that the hygromycin-resistance gene be flanked with lox71 and loxP. As a result, after completion of the gene targeting, the selection marker can be removed from the genome by transient expression of Cre. However, this is not the sole means for removing the marker. Other target sequences of site-specific recombinases, such as other lox sequences or FRT sequences, may also be used.

If desired, a splice acceptor site (SA site) may be introduced into the entry clone pENTR IRES-Hyg. By introducing the splice acceptor site, a reverse primer for 5'-arm amplification can be placed in an intron (not in an exon).

Figure 6:
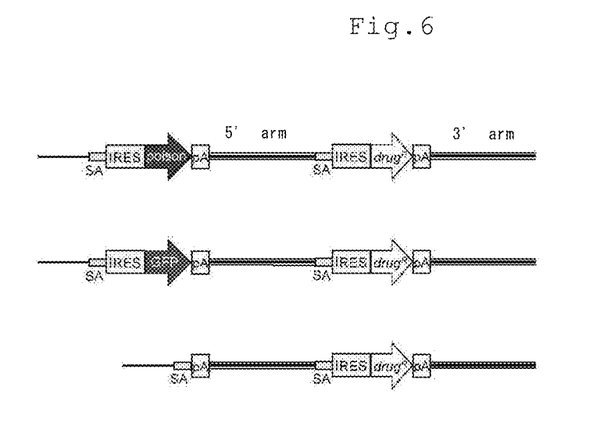
FIG. 6 shows an exemplary structure of the exon-trapping-type targeting vector having a cassette for negative selection that can be used in gene targeting based on the ExTraPNS method. Instead of a suicide gene shown in the upper diagram, a fluorescent protein gene (here, a GFP gene) can also be used (middle diagram). Alternatively, merely a splice acceptor sequence may be added upstream of the 5'-arm (lower diagram).

As a result of adding the SA-IRES-DTA-polyA cassette upstream of the 5'-arm, another (i.e., DTA) SA is located more upstream than SA of the positive selection marker. This considerably decreases the chance that randomly inserted clones acquire drug resistance (FIG. 5). Instead of the DTA gene, any of other suicide genes (e.g., an HSV-TK gene) or any of other genes such as a fluorescent protein marker (e.g., a GFP gene or a DsRed gene) may be used. Alternatively, the SA-polyA cassette can be merely added without inserting any of such genes (or IRES) (FIG. 6).

If a negative selection marker (e.g., a suicide gene such as a DTA gene or a fluorescent protein gene such as a GFP gene) is to be introduced into the cassette for negative selection, a DNA sequence that allows for bicistronic expression such as an IRES or 2A peptide sequence is preferably added. If, on the other hand, neither gene nor cDNA is to be introduced into the cassette for negative selection, there is no need to add the DNA sequence that allows for bicistronic expression.

While the production of a targeting vector (specifically, a step of linking a 5' arm, a selection marker, and a 3' arm) has been explained above taking the case of employing the MultiSite Gateway system as an example, this is not the sole linking method to be employed. That is, it is also possible to produce targeting vectors by other molecular biological methods or by using other items (for example, general methods using restriction enzymes or DNA ligase, In-Fusion PCR Cloning, etc.). Also, as a base for targeting vector construction without the use of entry clones (namely, the Gateway system), a plasmid in which a selection marker is flanked by multiple restriction sites may be used, as these sites permit incorporation of 5' and 3' arms, as well as vector linearization.

Gene knockout cells can be produced by introducing a genetic mutation into a cell with the use of gene targeting vectors constructed based on the present invention. Such gene knockout cells can be produced by previously described methods (for example, Adachi, N, So, S, Iiizumi, S, et al. (2006) The human pre-B cell line Nalm-6 is highly proficient in gene targeting by homologous recombination. DNA Cell Biol. 25: 19-24; Adachi, N, Nishijima, H, Shibahara, K (2008) Gene targeting using the human Nalm-6 pre-B cell line. BioScience Trends. 2: 169-180; Toyoda, E, Kagaya, S, Cowell, I G, et al. (2008) NK314, a topoisomerase II inhibitor that specifically targets the alpha isoform. J. Biol. Chem. 283: 23711-23720). To explain briefly, a targeting vector is linearized with a restriction enzyme, the linearized vector is then transfected into cells according to a gene transfer method such as electroporation, and the cells are then allowed for colony formation. Subsequently, cells into which a genetic mutation has been introduced are selected, using a marker as appropriate. In order to obtain cells into which a genetic mutation has been homozygously introduced (homozygously disrupted cell line), a second gene targeting may be carried out using a targeting-vector with a different selection marker. In addition, such selection markers can be removed by site-specific recombinase, for example, by transiently expressing Cre recombinase with the use of pBS185 plasmid. Additional mutations can be introduced into the cells from which the selection marker has been removed. Examples of the cells suitable for use in gene targeting include, but are not limited to, human Nalm-6 cells, chicken DT40 cells, and mouse ES cells. Rather, the present invention facilitates gene targeting even on general human cell lines. Hereinafter, experiments using a human fibrosarcoma-derived cancer cell line HT1080 (available from Health Science Research Resource Bank; http://www.jhsf.or.jp/cgi-bin/HSRRB/C_ViewDetail.cgi?jcrb=IFO50354) will be described in detail. The present invention is not limited by these examples.

EXAMPLE 1

Hereinafter, the present invention will be described in detail by means of Examples. However, these Examples are not intended to limit the scope of the present invention.

EXAMPLE 1

(Materials and Methods)
Construction of Target Vector
Materials
1. ExTaq™ polymerase (TAKARA BIO, INC.)
2. PCR primers: (for use in the amplification of the HPRT gene)

```
Primers for amplification of the 5' arm
(1)
HPRT 5'Fw,
                                        (SEQ ID NO: 1)
5'-GGGGACAACTTTGTATAGAAAAGTTGCACATCACAGGTACCATATC

AGTG-3';

(2)
HPRT 5' Rv (placed on the exon),
                                        (SEQ ID NO: 2)
5'-GGGGACTGCTTTTTTGTACAAACTTGCACATCTCGAGCAAGACGTT

CAGT-3';

Primer for amplification of the 3' arm
(3)
HPRT 3'Fw,
                                        (SEQ ID NO: 3)
5'-GGGGACAGCTTTCTTGTACAAAGTGGCCTGCAGGATCACATTGTAG

CCCTCTGTGTGC-3';

(4)
HPRT 3' Rv (to which an I-SceI site serving as
a restriction site for linearization has been
added),
                                        (SEQ ID NO: 4)
5'-GGGGACAACTTTGTATAATAAAGTTGCTATATTACCCTGTTATCCC

TAGCGTAACTCAGGGTAGAAATGCTACTTCAGGC-3'
```

3. MultiSite Gateway (registered trademark) Three Fragment Vector Construction Kit (Invitrogen)
4. Entry clone (pENTR IRES-Hyg) into which a drug resistance gene has been incorporated
   pENTR IRES-Hyg was produced by digesting the plasmid pENTR loxP (Iiizumi, S, Nomura, Y, So, S, et al. (2006) Simple one-week method to construct gene-targeting vectors: application to production of human knockout cell lines. Biotechniques 41: 311-316) with NotI, and then a cassette comprising lox71, IRES, Hyg, pA, and loxP was added to the digested plasmid. In this process, lox71 and loxP were added to the plasmid using synthetic linker DNA; IRES and pA were derived from the vector pIRES (TAKARA BIO, INC.; http://catalog.takara-bio.co.jp/product/basic_info.asp?unitid=U100004407); and Hyg was derived from pENTR lox-Hyg (Iiizumi, S, Nomura, Y, So, S, et al. (2006) Simple one-week method to construct gene-targeting vectors: application to production of human knockout cell lines. Biotechniques 41: 311-316.)
5. Destination vector (pDEST R4-R3) (Invitrogen)
6. Destination vector (pDEST R4-R3 SA-IRES-DTA-pA)
   pDEST R4-R3 SA-IRES-DTA-pA was prepared by the following procedures:
   1. PCR was performed using primers DTA-Sal Fw (5'-GTCGACATGGATCCTGATGATGTTGTTGAT-3') (SEQ ID NO: 7) and DTA-Not Rv (5'-GCGGCCGCTTAGAGCTTTAAATCTCTGTAGGTA-3') (SEQ ID NO: 8). The obtained DTA-gene fragment was subcloned into the NotI site of a pIRES vector (Clontech Laboratories, Inc., Cat. No. 631605). This PCR was performed using KOD-Plus-DNA polymerase (TOYOBO CO., LTD.) under the following conditions:
   94° C. for 2 min
   94° C. for 30 sec
   65° C. for 30 sec×35 cycles
   68° C. for 40 sec
   68° C. for 7 min
   2. A pSAβgeo plasmid (Friedrich, G. & Soriano P. Genes Dev. 5, 1513-1523, 1991) was digested with BamHI and blunt-ended using (the 以下同様) Klenow Fragment. Then, the resulting fragment of approximately 200 by containing an SA site (derived from an adenovirus type 2 major late transcript splice acceptor) was added to a region upstream (XhoI site; blunt-ended using Klenow Fragment) of the IRES sequence in the vector prepared in the preceding step 1.
   3. The plasmid prepared in the preceding step 2 was digested with BglII and PvuI and blunt-ended. Then, the resulting DNA fragment containing SA-IRES-DTA-pA was added to an AflIII site (blunt-ended using Klenow Fragment) in a pDEST R4-R3 plasmid (Invitrogen Corp.).
7. Antibiotic-containing LB agar medium: LB agar medium containing 50 µg/ml kanamycin or 50 µg/ml ampicillin
Protocols
1. With human genomic DNA as a template, PCR was carried out under the following conditions, so as to obtain an HPRT genomic fragment flanked with attB sequences. Primers (1) and (2) were used to amplify the 5' arm, whereas primers (3) and (4) were used to amplify the 3' arm.

TABLE 1

| | | |
|---|---|---|
| 94° C. | 2 minutes | |
| 94° C. | 40 seconds | |
| 68° C. | 1 minute | ] 35 cycles |
| 72° C. | 3 minutes | |
| 72° C. | 7 minutes | |

2. The obtained PCR product was purified with a commercially available kit, and was then quantified.
3. A BP recombination reaction was carried out to produce a 5'-entry clone and a 3'-entry clone (FIG. 2A). The following samples were mixed in a 0.5-ml tube.

| | |
|---|---|
| pDONR P4-P1R or pDONR P2R-P3 | 50 fmoles |
| 5' or 3' arm fragment | 50 fmoles |
| Total amount | 8 μl (prepared with TE solution) |

4. 1μl of BP Clonase II Enzyme Mix was added to 4 μl of the aforementioned reaction solution, and mixed well.

5. The mixture was incubated at 25° C. for 4 to 5 hours.

6. 1 μl of 2 μg/μl proteinase K was added to the reaction mixture, and mixed well.

7. The resultant mixture was incubated at 37° C. for 10 minutes.

8. 5 μl of the reaction solution was mixed with 50 μl of *Escherichia coli* competent cells to carry out transformation. After completion of a recovery culture, cells were plated on an LB agar medium containing 50 μg/ml kanamycin.

9. Five to ten kanamycin-resistant colonies were isolated, and plasmid DNA was then extracted from the colonies according to an alkali-SDS method. Two or three clones predicted to contain plasmids of interest were then selected by agarose gel electrophoresis. These candidate plasmids were digested with appropriate restriction enzymes, and were then subjected to agarose gel electrophoresis, whereupon they were confirmed to be the plasmids of interest.

10. The obtained 5' and 3' entry clones were purified with a commercially available kit and quantified.

11. A targeting vector (pHPRT-IRES-Hyg) was produced by an LR recombination reaction (FIG. 2B). Respective samples were mixed in a 0.5-ml tube as follows.

| | |
|---|---|
| pDEST R4-R3 or pDEST R4-R3 SA-IRES-DTA-pA | 20 fmoles |
| 5'-Entry clone | 10 fmoles |
| 3'-Entry clone | 10 fmoles |
| pENTR IRES-Hyg | 10 fmoles |
| Total amount | 8 μl (prepared with TE solution) |

12. 1 μl of LR-Clonase Plus Enzyme Mix was added to 4 μl of the aforementioned reaction solution, and mixed well.

13. The mixture was incubated at 25° C. for 16 hours.

14. 1 μl of 2 μg/μl proteinase K was added to the reaction mixture, and mixed well.

15. The resultant mixture was incubated at 37° C. for 10 minutes.

16. 5 μl of the reaction solution was mixed with 50 μl of *Escherichia coli* competent cells to carry out transformation. After completion of a recovery culture, cells were plated on an LB agar medium containing 50 μg/ml ampicillin.

17. Five to Ten ampicillin-resistant colonies were isolated, and plasmid DNA was then extracted from the colonies according to an alkali-SDS method. Two or three clones predicted to contain plasmids of interest were then selected by agarose gel electrophoresis. These candidate plasmids were digested with appropriate restriction enzymes, and were then subjected to agarose gel electrophoresis, whereupon they were confirmed to be the plasmids of interest (namely, targeting vectors).

18. The obtained targeting vectors were purified and quantified.

Linearization of Targeting Vector

Materials

1. Restriction enzyme I-SceI, 10× I-SceI reaction buffer, 10 mg/ml BSA (New England Biolabs)

2. 3 M sodium acetate: 40.81 g of sodium acetate was dissolved in 80 ml of pure water. Then, the solution was pH-adjusted to 5.2 with acetic acid, and its total amount was adjusted to 100 ml.

3. TE solution: 10 mM Tris-HCl buffer (pH 8.0), 0.1 mM EDTA (pH 8.0) (stored at 4° C.)

Protocols

1. The targeting vector was digested with the restriction enzyme I-SceI. Individual reagents were mixed together as follows, and the obtained mixture was then incubated at 37° C. for at least 4 hours.

| | |
|---|---|
| Targeting vector | 50 μg |
| 10× I-SceI buffer | 40 μl |
| 100× BSA (10 mg/ml) | 4 μl |
| I-SceI | 15 units |
| Total amount | 400 μl (prepared with sterilized water) |

2. 40 μl of 3 M sodium acetate and 0.9 ml of ethanol were added to the reaction solution, and mixed well.

3. The mixture was centrifuged at 15,000 rpm for 5 minutes.

4. The pellet was washed with 0.5 ml of 70% ethanol three times.

5. After completion of the $3^{rd}$ centrifugation, supernatants were removed using a sterilized tip in a clean bench, followed by air-drying.

6. A TE solution was added to dissolve DNA (to a DNA concentration of 2 to 4 μg/μl).

7. The solution was incubated at 65° C. for 15 minutes.

Gene Transfer by Electroporation and Colony Formation

Materials

1. Growth medium: A medium prepared by adding 10% fetal bovine serum (HyClone) to ES medium (NISSUI PHARMACEUTICAL CO., LTD.). The prepared medium was kept warm at 37° C. in a hot water bath.

2. Linearized targeting vector

3. Cell Line Nucleofector (registered trademark) Kit T (Lonza Group Ltd.)

4. Selection drug (100 mg/ml hygromycin B): 1 g of hygromycin B dissolved in 10 ml of pure water and sterilized by filtration (stored at 4° C.)

Protocols

1. Human HT1080 cells (>$2\times10^6$ cells) that were at a logarithmic growth phase were recovered in a 50-ml centrifugal tube.

2. The cells were centrifuged at 1,100 rpm for 5 minutes, and supernatants were gently removed.

3. 100 μl of Solution T was added to the cell mass, and the cells were counted.

4. Cells ($2\times10^6$) were mixed with 2 μg of the linearized targeting vector, and the amount of the mixture was adjusted to 100 μl with Solution T, followed by transfer to a dedicated cuvette.

5. The cuvette was fitted onto an electroporation device (Nucleofector II, Lonza).

6. Program L-005 was executed.

7. The cells were immediately transferred into a 60-mm dish that contained 4 ml of growth medium.

8. 1 ml aliquots of the cell suspension were transferred to 90-mm dishes (×4) containing 9 ml of the growth medium.

9. The cells were cultured at 37° C. for 48 hours.

10. After trypsin treatment, the cells were recovered by centrifugation at 1,100 rpm for 5 minutes.
11. The cells were suspended in an appropriate amount of the growth medium, and counted.
12. The cells were inoculated at a density of 2 to $4 \times 10^5$ cells/dish on 90-mm dishes (each containing 9 ml of the growth medium).
13. After culture at 37° C. for 24 hours, 25 to 40 µl of the selection drug (100 mg/ml hygromycin) was added thereto.
14. The cells were cultured at 37° C. for 2 weeks to form colonies.

Isolation of Colonies and Selection of Targeted Clones
Materials
1. Selection medium (hygromycin B-containing medium): growth medium supplemented with hygromycin B to a concentration of 0.25 to 0.4 mg/ml
2. 0.1% trypsin solution: 0.1% trypsin/0.02% EDTA/PBS⁻
3. Lysis buffer: 20 mM Tris-HCl buffer (pH 8.0), 250 mM sodium chloride, 1% SDS
4. 10 mg/ml proteinase K: 100 mg of proteinase K as dissolved in 10 ml of pure water and then sterilized by filtration (stored at −20° C.)
5. Saturated NaCl solution
6. ExTaq™ polymerase
7. PCR primers: (used for confirmation of HPRT gene targeting; Iiizumi et al. Nucleic Acids Res., 2008, November; 36(19): 6333-6342.)

```
HPRT-F,
                                     (SEQ ID NO 5)
5'-TGAGGGCAAAGGATGTGTTACGTG-3'

HPRT-R,
                                     (SEQ ID NO 6)
5'-TTGATGTAATCCAGCAGGTCAGCA-3'
```

Protocol
1. 1.5 ml of the selective medium and 0.75 ml of the growth medium were each dispensed in wells of 24-well plates.
2. After treatment with the 0.1% trypsin solution, the cells were transferred to the well containing 1.5 ml of the selective medium (for genome extraction) by gently pipetting.
3. From the 24-well plate to which the cells had been transferred, 0.25 ml of the cell suspension was taken out and transferred to the well containing 0.75 ml of the growth medium (for subculture).
4. The cells were cultured at 37° C. for 2 to 3 days.
5. To extract genome DNA, the culture medium in each well of the 24-well plate was removed. Then, 250 µl of the lysis buffer and 1 µl of 10 mg/ml proteinase K were added to the cells, and the mixture was transferred to a 1.5-ml tube, while pipetting was fully performed.
6. The mixture was incubated overnight at 37° C. (or at 55° C. for 1 hour).
7. 80 µl of the saturated NaCl solution was added to the reaction mixture and mixed well.
8. 250 µl of 2-propanol was further added to the reaction mixture and mixed well.
9. The reaction mixture was centrifuged at 15,000 rpm at 4° C. for 15 minutes.
10. The precipitates were removed and washed with 0.5 ml of 70% ethanol.
11. The precipitates were dissolved in 30 to 100 µl of TE solution.
12. PCR was performed with the prepared genomic DNA as a template using the primers HPRT-F and HPRT-R under the following reaction conditions to screen for the targeted clones:

TABLE 2

| | | |
|---|---|---|
| 94° C. | 2 minutes | |
| 94° C. | 40 seconds | |
| 60° C. | 1 minute | 35 cycles |
| 72° C. | 2 minutes and 20 seconds | |
| 72° C. | 7 minutes | |

A puromycin-resistance gene or a fusion gene of a β-galactosidase gene with a neomycin-resistance gene can be substituted for the hygromycin-resistance gene. Using such drug-resistance genes, the aforementioned reactions were repeated.

In addition, an IRES2 sequence or a 2A peptide sequence can be substituted for the IRES sequence as a DNA sequence allowing for bicistronic expression. Using these sequences, the aforementioned reactions were repeated.

Clones that were positive in PCR screening should be then subjected to Southern blot analysis in order to confirm that they have undergone correct homologous recombination reaction.

(Results)
The results of gene targeting using human HT1080 cells are summarized in a table that follows. For "Negative selection (DT-A): Present", a targeting vector having an SA-IRES-DTA-pA cassette added upstream of the 5'-arm was used.

TABLE 3

| | Targeting vector | Negative selection (DT-A) | Targeting efficiency (%) | Relative random insertion frequency |
|---|---|---|---|---|
| Experiment 1 | HPRT-IRES-Hyg | Absent | 0 (0/133) | 1 |
| | | Present | 3.7 (1/27) | 0.13 |
| Experiment 2 | HPRT-2A-Puro | Absent | 1.7 (2/116) | 1 |
| | | Present | 4.7 (2/43) | 0.049 |
| Experiment 3 | HPRT-2A-eGFP-2A-Puro | Absent | 0.4 (1/250) | 1 |
| | | Present | 3.6 (2/55) | 0.076 |

These results demonstrate that by using an exon-trapping-type targeting vector and introducing thereinto a cassette for negative selection, gene targeting can be performed with high efficiency, as random insertion frequency is significantly reduced.

All publications, patents and patent applications cited herein are incorporated herein by reference in their entirety.

Industrial Applicability
The present invention is effective for enabling a wider and/or more efficient use of gene knockout or gene trapping in the fields of basic biology, medicine, and agriculture & livestock industries.

Sequence Listing Free Text
<SEQ ID NO: 1>
SEQ ID NO: 1 shows the DNA sequence of a forward primer for amplification of a 5' arm that targets the human HPRT gene. 5'-GGGG<u>ACAACTTTGTATAGAAAAGTTG</u>CACATCACAGGTACCATATCAGTG-3'
(The underlined portion indicates the attB4 sequence.)
<SEQ ID NO: 2>
SEQ ID NO: 2 shows the DNA sequence of a reverse primer for amplification of a 5' arm that targets the human HPRT gene. 5'-GGGG<u>ACTGCTTTTTTGTACAAACTTG</u>CACATCTCGAGCAAGACGTTCAGT-3'
(The underlined portion indicates the attB1 sequence.)
<SEQ ID NO: 3>
SEQ ID NO: 3 shows the DNA sequence of a forward primer for amplification of a 3' arm that targets the human HPRT gene. 5'-GGGGACAGCTTTCTTGTACAAAGTGG
CCTGCAGGATCACATTGTAGCCCTCTGTGTGC-3'
(The underlined portion indicates the attB2 sequence.)
<SEQ ID NO: 4>
SEQ ID NO: 4 shows the DNA sequence of a reverse primer for amplification of a 3' arm that targets the human HPRT gene. 5'-GGGGACAACTTTGTATAATAAAGTTG
CTATATTACCCTGTTATCCCTAGCG-
TAACTCAGGGTAGAAATGCTACTTCAGGC-3'
(The underlined portion indicates the attB3 sequence.)
<SEQ ID NO: 5>
SEQ ID NO: 5 shows the DNA sequence of a PCR primer (HPRT-F) for confirmation of gene targeting.
HPRT-F, 5'-TGAGGGCAAAGGATGTGTTACGTG-3'

<SEQ ID NO: 6>
SEQ ID NO: 6 shows the DNA sequence of a PCR primer (HPRT-R) for confirmation of gene targeting.
HPRT-R, 5'-TTGATGTAATCCAGCAGGTCAGCA-3'
<SEQ ID NO: 7>
SEQ ID NO: 7 shows the DNA sequence of the primer DTA-Sal Fw (5'-GTCGACATGGATCCTGATGATGTTGT-TGAT-3').
<SEQ ID NO: 8>
SEQ ID NO: 8 shows the DNA sequence of the primer DTA-Not Rv (GCGGCCGCTTAGAGCTTTAAATCTCTG-TAGGTA).

The invention claimed is:

1. A gene targeting vector comprising
   i) a nucleic acid sequence encoding a positive selection marker flanked by DNA homologous to a 5'-upstream and a 3'-downstream homology arm (FIG. 2; pg 6, 1st full paragraph), wherein the nucleic acid sequence encoding a positive selection marker is not operably linked to a promoter;
   ii) a nucleic acid sequence encoding a negative selection marker introduced 5' upstream of the 5'-upstream homology arm; wherein the nucleic acid sequence encoding the negative selection marker is operably linked to:
      a) a splice acceptor site; and
      b) a DNA sequence allowing for bicistronic expression.

2. The vector according to claim 1, wherein a poly-A sequence is added to the positive selection marker.

3. The vector according to claim 1 or 2, wherein a poly-A sequence is added to the negative selection marker.

4. The vector according to claim 1, wherein a restriction site(s) for linearization is further introduced in the vector.

5. A method for preparing a gene knockout cell line, comprising introducing a genetic mutation to a cell using a gene targeting vector according to claim 1.

6. A gene knockout cell prepared by the method of claim 5.

* * * * *

SEQUENCE LISTING

```
<160> NUMBER OF SEQ ID NOS: 8

<210> SEQ ID NO 1
<211> LENGTH: 50
<212> TYPE: DNA
<213> ORGANISM: Artificial
<220> FEATURE:
<223> OTHER INFORMATION: HPRT 5' Fw primer

<400> SEQUENCE: 1
ggggacaact ttgtatagaa aagttgcaca tcacaggtac catatcagtg          50

<210> SEQ ID NO 2
<211> LENGTH: 50
<212> TYPE: DNA
<213> ORGANISM: Artificial
<220> FEATURE:
<223> OTHER INFORMATION: HPRT 5' Rv primer

<400> SEQUENCE: 2
ggggactgct tttttgtaca aacttgcaca tctcgagcaa gacgttcagt          50

<210> SEQ ID NO 3
<211> LENGTH: 58
<212> TYPE: DNA
<213> ORGANISM: Artificial
<220> FEATURE:
<223> OTHER INFORMATION: HPRT 3' Fw primer

<400> SEQUENCE: 3
ggggacagct tcttgtaca aagtggcctg caggatcaca ttgtagccct ctgtgtgc   58

<210> SEQ ID NO 4
<211> LENGTH: 80
<212> TYPE: DNA
<213> ORGANISM: Artificial
<220> FEATURE:
<223> OTHER INFORMATION: HPRT 3' Rv primer

<400> SEQUENCE: 4
ggggacaact tgtataata aagttgctat attaccctgt tatccctagc gtaactcagg 60
gtagaaatgc tacttcaggc                                            80

<210> SEQ ID NO 5
<211> LENGTH: 24
<212> TYPE: DNA
<213> ORGANISM: Artificial
<220> FEATURE:
<223> OTHER INFORMATION: HPRT-F primer

<400> SEQUENCE: 5
```

```
tgagggcaaa ggatgtgtta cgtg                                                      24

<210> SEQ ID NO 6
<211> LENGTH: 24
<212> TYPE: DNA
<213> ORGANISM: Artificial
<220> FEATURE:
<223> OTHER INFORMATION: HPRT-R primer

<400> SEQUENCE: 6
ttgatgtaat ccagcaggtc agca                                                      24

<210> SEQ ID NO 7
<211> LENGTH: 30
<212> TYPE: DNA
<213> ORGANISM: Artificial Sequence
<220> FEATURE:
<223> OTHER INFORMATION: DTA-Sal Fw primer

<400> SEQUENCE: 7
gtcgacatgg atcctgatga tgttgttgat                                                30

<210> SEQ ID NO 8
<211> LENGTH: 33
<212> TYPE: DNA
<213> ORGANISM: Artificial Sequence
<220> FEATURE:
<223> OTHER INFORMATION: DTA-Not Rv primer

<400> SEQUENCE: 8
gcggccgctt agagctttaa atctctgtag gta                                            33
```